US007189761B2

(12) United States Patent
Gorfine

(10) Patent No.: US 7,189,761 B2
(45) Date of Patent: *Mar. 13, 2007

(54) NITRIC OXIDE DONOR COMPOSITION AND METHOD FOR TREATMENT OF ANAL DISORDERS

(76) Inventor: Stephen R. Gorfine, 25 E. 69th St., New York, NY (US) 10021

( * ) Notice: Subject to any disclaimer, the term of this patent is extended or adjusted under 35 U.S.C. 154(b) by 0 days.

This patent is subject to a terminal disclaimer.

(21) Appl. No.: 10/669,099

(22) Filed: Sep. 22, 2003

(65) Prior Publication Data

US 2005/0075391 A1    Apr. 7, 2005

Related U.S. Application Data

(63) Continuation of application No. 10/021,168, filed on Dec. 11, 2001, now abandoned, which is a continuation of application No. 08/970,447, filed on Nov. 14, 1997, now abandoned, which is a continuation of application No. 08/666,264, filed on Jun. 20, 1996, now Pat. No. 5,693,676, which is a continuation of application No. 08/371,088, filed on Jan. 10, 1995, now abandoned, which is a continuation-in-part of application No. 08/250,555, filed on May 27, 1994, now Pat. No. 5,504,117.

(51) Int. Cl.
*A61K 31/04* (2006.01)

(52) U.S. Cl. .................. 514/742; 514/470; 514/740; 514/171; 514/179; 514/312; 514/882; 514/929

(58) Field of Classification Search .............. 514/742, 514/470, 740, 171, 179, 312, 882, 969
See application file for complete search history.

(56) References Cited

U.S. PATENT DOCUMENTS

| 814,408 | A |   | 3/1906 | Steele |
|---|---|---|---|---|
| 2,840,080 | A |   | 6/1958 | Clark |
| 3,419,571 | A |   | 12/1968 | Di Carlo et al. |
| 4,118,480 | A |   | 10/1978 | Williams |
| 4,226,849 | A | * | 10/1980 | Schor .................. 424/469 |
| 4,292,299 | A |   | 9/1981 | Suzuki et al. |
| 4,371,516 | A | * | 2/1983 | Gregory et al. ........ 424/485 |
| 4,514,384 | A | * | 4/1985 | Gallina .................. 514/179 |
| 4,608,249 | A |   | 8/1986 | Otsuka et al. |
| 4,654,209 | A | * | 3/1987 | Leslie et al. ........... 424/78.25 |
| 4,657,906 | A |   | 4/1987 | Emmett et al. |
| 4,683,242 | A |   | 7/1987 | Poser |
| 4,746,675 | A |   | 5/1988 | Makino et al. |
| 4,842,854 | A | * | 6/1989 | Babaian et al. ........ 424/78.18 |
| 5,047,230 | A | * | 9/1991 | Nagy et al. ............ 424/45 |
| 5,059,603 | A |   | 10/1991 | Rubin |
| 5,085,650 | A | * | 2/1992 | Giglio .................. 604/288 |
| 5,183,663 | A |   | 2/1993 | Greiner |
| 5,439,938 | A | * | 8/1995 | Snyder et al. .......... 514/565 |
| 5,504,117 | A | * | 4/1996 | Gorfine ................ 514/742 |
| 5,508,045 | A |   | 4/1996 | Harrison et al. |
| 5,595,753 | A | * | 1/1997 | Hechtman ............. 424/436 |
| 5,595,970 | A | * | 1/1997 | Garfield et al. ....... 514/12 |
| 5,693,676 | A | * | 12/1997 | Gorfine ................ 514/742 |
| 5,827,889 | A | * | 10/1998 | Cunico ................. 514/565 |

FOREIGN PATENT DOCUMENTS

| AU | PM 6395 | 7/1994 |
|---|---|---|
| AU | 74545/94 | 8/1994 |
| AU | PM 0971 | 3/1995 |
| AU | PM 4247 | 3/1995 |
| DE | 304730 | 3/1989 |
| DE | 4038203 | 6/1992 |
| JP | 62-67017 | 3/1987 |
| JP | 04-091036 | 3/1996 |
| WO | WO 87/03490 | 6/1987 |
| WO | WO 95/06466 A1 | 3/1995 |
| WO | WO 98/36733 | 8/1998 |
| WO | WO 98/37886 | 9/1998 |
| ZA | 77/01135 | 2/1977 |
| ZA | 9500511 A | 3/1996 |

OTHER PUBLICATIONS

Loder et al. "Topical Application of Nitric Oxide Donor Reduces Internal Anal Sphincter Tone: Therapeutic Implications". Gut. Apr. 1993. Abstract S25 (T96).*

Loder et al. "Topical Glyceryl Trinitrate (GTN): Reversible Chemical Sphicterotomy". Am Society of Colon and Rectal Surgeons 92nd An Conv Podium and Poster Abstracts, Chicago, IL. May 2-7, 1993. Dis Colon Rectum Meeting Abstrs, Apr. 1993, P22(64).*

(Continued)

*Primary Examiner*—Christopher R. Tate
(74) *Attorney, Agent, or Firm*—Townsend and Townsend and Crew LLP

(57) ABSTRACT

A pharmaceutical composition contains a nitric oxide donor and advantageously an optional corticosteroid and/or topical anesthetic. The composition is useful in a method for treating anal disorders such as anal fissure, anal ulcer, hemorrhoidal disease, levator spasm, and so forth, by topical application to or proximate the affected area.

26 Claims, No Drawings

OTHER PUBLICATIONS

Guillemot et al. "Action of in Situ Nitroglycerin on Upper Anal Canal Pressure of Patients with Terminal Constipation—A Pilot Sudy". Dis. Colon Rectum. Apr. 1993, pp. 372-376.*

Jensen, S. "Treatment of First Episodes of Acute Anal Fissure: Prospective Randomised Study of Lignocaine Ointment Vs. Hydrocortisone Olntment or Warm Sitz Baths Plus Bran". 1996.*

Ahlner et al., "Organic Nitrate Esters: Clinical Use and Mechanisms of Actions." *Pharmacol. Reviews* 43(3):351-353 (1991).

Budavari et al. (Eds.), "The Merck Index." pp. 198 and 821 (isopropyl nitrate); 11th Edition, Merck & Co., Rahway, N.J. (1989).

Bult et al., "Nitric oxide as an inhibitory non-adrenergic non-cholinergic neurotransmitter." *Nature*, 345:346-347, 1990.

Burleigh, D. and D'Mello, A., "Physiology and Pharmacology of the Internal Anal Sphincter." Chapter 2, pp. 22-41, in *Coloproctology and The Pelvic Floor*, Henry and Swash (Eds.), Butterworth Publishers, Stoneham, Mass., USA and London, England, ISBN 0-407-00352-5 (1985).

Burleigh, D., "Ng-Nitro-L-Arginine Reduces Nonadrenergic Relexations of Human Gut." *Gastroenterology*, 102: 679-683 (1992).

Chakder, et al. "Release of nitric oxide by activation of nonadrenergic honcholinergic neurons of internal anal sphincter." *NO Release By Nanc Naural Simulation and VIP*, G7-12 (1992).

Enck et al., "Spontaneous variation of anal 'resting' pressure in healthy humans." *Am. J. Physiol.*, 261(5 Pt 1):G823-G826 (1991).

Farouk et al., "Sustained Internal Sphincter Hypertonia in Pa7tients with Chronic Anal Fissure." *Dis. Col. Rect.*, 37:424-429 (1994).

Feelisch et al., "Correlation between nitric oxide formation during degradation of organic nitrates and activation of guanylate cyclase." *Eur. J. Pharmacol.*, 139:19-30 (1987).

Fung et al., "Biochemical mechanism of organic nitrate action." *Am. J. Cardiol.*, 70:4B-10B (1992).

Gibbons et al., "Anal hypertonia in fissures; cause or effect?" *Br. J. Surg.*, 73:443-445 (Jun. 1986).

Gillespie et al., "Influence of hemoglobin and erythrocytes on the effects of EDRF, a smooth muscle inhibitory factor, and nitric oxide on vascular and non-vascular smooth muscle." *Br. J. Pharmacol.*, 95:1151-1156, 1988.

Gorfine, SR., 1995, "Treatment of benign anal disease with topical nitroglycerin." *Dis. Col. Rect.*, 38(5):453-456.

Guillernot et al., "Nitroglycerin In Situ Reduces Upper Anal Cause Pressure." *Digest. Dis. Sci.*, 37(1):155 (1992).

Guillernot et al., "Action of *in situ* nitroglycerin on upper anal canal pressure of patients with terminal constipation. A pilot study." *Dis. Col. Rect.*, 36(4):372-376 (1993).

Huff et al., (Eds.), "Physician' Desk Reference." 41st Edition, Medical Economics Company, Oradell, N.J., at pp. 780, 1176-1178, 1533 and 1984-85 (1987).

Ignarro et al., "Nitric oxide and cyclic GMP formation upon electrical field stimulation cause relaxation of corpus cavernosum smooth muscle." *Biochem. Biophys. Res. Commun.*, 170:843-850, 1990.

Jalan, K. et al., "Perineal Wound Healing in Ulcerative Colitis." *British Journal of Surgery* (Oct. 1969) 56(10):749-53.

Jensen, S. "Treatment of first episodes of acute anal fissure: Prospective radomized study of lignocaine ointment versus hydrocortisone ointment or warm sitz bath plus bran." *Br. Med. J.*, 292(6529):1167-9 (1986).

Keigthley, R. and Williams, N.."Anatomy and Physiology." Chapter One, in *Surgery of the Anus, Rectum and Colon*, London, W.B. Saunders (1993).

Kennedy, M. et al, "Chemical Sphincterotomy for Anal Fissure—A New Treatment." Abstract CR33, presentation at Royal Australasian College of Surgeons at Hobart, Tasmania meeting of May 1-6, 1994.

Kennedy, M. et al., "Glyceryl Trinitrate Ointment for the Treatment of Chronic Anal Fissure." *Dis Colon Rectum* 42(8):1000-1006 (Aug. 1999).

Loder, P. et al, "'Reversible chemical sphincterotomy' by local application of glyceryl trinitrate." *Br. J. Surg.*, 81: 1386-1389 (1994).

Loder, P. et al, "Topical Application of a Nitric Oxide Donor Reduces Internal Anal Sphincter Tone: Therapeutic Implications." *Gut* 34:S25 (1993) Abstract also published in *AGA Abstracts, Gastroenterology*, 104: A544 (1993).

Loder, P. et al., "Topical Glyceryl Trinitrate (GTN): Reversible Chemical Sphincterotomy." Meeting Abstracts. *Dis. Col. Rect.*, 33:22 (Apr. 1993).

Lord, P., "A Day-Case Procedure for the Cure of Third-Degree Haemorrhoids." *Br. J. Surg.* 56(10):47-9 (1969).

Lubowski, D. et al., "Neural control of internal anal sphincter function." *Br. J. Surg.* 74: 668-670 (Aug. 1987).

Lund, J. and Scholefield, J., "A randomised, prospective, double-blind, placebo-controlled trial of glyceryl trinitrate ointment in treatment of anal fissure." *Lancet*, 349: 11-14 (Jan. 4, 1997).

Lund, J. et al., "Use of glyceryl trinitrate ointment in the treatment of anal fissure." British Journal of Surgery 83: 776-777 (1996).

MacDonald, A. et al., "Manual dilation of the anus." *British Journal of Surgery* 79:1381-1382 (Dec. 1992).

*Mims Annual Drug Reference*, Fifteenth Edition, 2-75, p. 2042 (1991).

O'Kelley, T. et al, "Nerve mediated relaxation of the human internal anal sphincter: the role of nitric oxide." *Gut*, 34: 689-693 (1993).

Rattan, S. and Chakder, S., "Role of nitric oxide as a mediator of internal anal sphincter relaxation." *Am. J. Physiol.* G107-G112 (1992).

Rattan, S. et al., "Nitric Oxide Pathway in Rectoanal Inhibitory Reflex of Opossum Internal Anal Sphincter." *Gastroenterology*, 103: 43-50 (1992).

Shafik, "Role of warm-water bath in anorectal conditions: the thermospheric reflex." *J. Clin. Gastroenterol.*, 16:304-8 (1993).

Schouten, W.R. et al. "Pathophysiological aspects and clinical outcome on intra-anal application of isosorbide dinitrate in patients with chronic anal fissure." *Gut* 39:465-9 (1996); see also: *Dis. Col. Rect.*, Apr. 1986, p. 18.

Speakman, C. et al., "Sphincter injury after anal dilation demonstrated by anal endosonography." *Br. J. Surg.*, 78: 1429-1430 (Dec. 1991).

Tottrup, A. et al., "Involvement of the L'Arginine-Nitric Oxide Pathway in Internal Anal Sphincter Relexation." *Gastroenterology*, 102: 409-41 (1992).

Watson, S.J. et al. "Topical glyceryl trinitrate in the treatment of chronic anal fissure." *Br. J. Surg.*, 83:771-775 (1996).

Abcarian, "The Role of internal spinchter in chronic anal fissures." *Dis. Col. Rect.*, 25(6) 525-8 (1982).

Bacher, H. et.al. "Local nitroglycerin for treatment of anal fissures: an alternative to lateral sphincterotomy?" *Dis. Col. Rect.*, 40:840-5 (1997).

Carapeti, E.A. et.al. "Randomised controlled trial shows that glyceryl trinitrate heals anal fissures, higher doses are not more effective, and there is high recurrence rate." *Gut*, 44:727-30 (1999).

Corby, "Anal canal pressures are low in women with postpartum anal fissure." *Br. J. Surg.*, 84:86-8 (1997).

*Dictionnaire Vidal*, Ed. 1996, entries concerning Lenitral Percutane and Lenitral Spray (1996).

Dodi, "Hot or cold in anal pain? A study of the changes in internal anal spinchter pressure profiles." *Dis. Col. Rect.*, 29(4):248-51 (1986).

Farid, M. "Internal anal sphincter relaxtion with topical nitroglycerin in the treatment of some benign anal conditions." *Br. J. Surg.*, 84:1 (1997).

Farouk, R. et al. "Changing patterns of treatment for chronic anal fissure." *Annual Review College Surgeons England*; 80:194-6 (1998).

"Glyceryl trinitrate for anal fissure?" *Drug and Therapeutics Bulletin*; 36:55-6 (1998).

Gorfine, S.R. "Topical nitroglycerin ointment for anal fissures and ulcers." *New England Journal of Medicine*; 333: 1156-7 (1995).

Hattori, K. et.al. "Fissure treatment in day surgery days." Presented at the *1998 General Assembly of The Japan Society of Coloproctology* (1998).

Hyman, N.H. et al. "Nitroglycerin ointment for anal fissures: Effective treatment or just a headache?" *Dis. Col. Rect.*, 42:383-5 (1999).

Keck, "Computer-generated profiles of the anal canal in patients with anal fissure." *Dis. Col. Rect.*, 38(1):72-9 (1995).

L'Hopital, "Constipation et hypertonie du sphincter Interne de l'anus: Response sphincterienne a l'administration sub-linguale de 0,40 mg de NATISPRAY." *Gastoentor. Clin. Biol.*, 14:268 (1990).

Lowenstein, B. et.al. Treatment of proctalgia fugax with topical nitroglycerin: report of a case. *Dis. Col. Rect.*; 41:667-8. (1998).

Lund JN et al. "Follow-up of patients with chronic anal fissure treated with topical glyceryl trinitrate." *Lancet*, 352:1681 (1998).

Lysy, J. et.al. "Treatment of chronic anal fissure with isosorbide dinitrate: long-term results and dose determination." *Dis. Col. Rect*, 41:1406-10 (1998).

Manookian, C.M. et al. Topical nitroglycerin in the management of anal fissure: an explosive outcome! *American Surgeon* 64:962-4 (1998).

Maria, "Identification of anti-endothelial cell antibodies in patients with chronic anal fissure." *Surgery*, 126:535-40 (1999).

Mazier, "Hemorrhoids, fissures, and pruritus ani." *Anorectal Surg.*, 74(6):1277-92 (1994).

Oettle, G.J. et.al. "Glyceryl trinitrate vs. sphincterotomy for treatment of chronic fissure-in-ano: a randomized, controlled trial." *Dis. Col. Rect.*, 40:1318-20 (1997).

Pitt, J. et.al. "Chemical sphincterotomy for anal fissure." *Colorectal disease* 1998; 2-8.

Pitt, "Double-blind, randomized, placebo-controlled trial of oral indoramin to treat chronic anal fissure." ASCRS Meeting, Jun. 2000, Poster Presentation P2 (2000).

Romano, "A critical appraisal of pathogenesis and morbidity of surgical treatment of chronic anal fissure." *J. Am. Coll. Surg.*, 178:600-4 (1994).

Schouten, "Relationship between anal pressure and anodermal blood flow: The vascular pathogenesis of anal fissures." *Dis. Col. Rect.*, 37(7):664-9 (1994).

Schouten, "Ischaemic nature of anal fissure." *Br. J. Surg.*, 83:63-5 (1996).

Simons, A.J. et al. "Glyceryl trinitrate for anal fissure." *Lancet*, 348:491-2 (1996).

Suda, K. et.al. "Application of nitroglycerin ointment on post-hemorrhoidectomy pain." Presented at the *1998 General Assembly of The Japan Society of Coloproctology* (1998).

Adams, M., Declaration of Dr. Michael Adams, including *Curriculum Vitae*, 22 pages, Mar. 13, 2006.

Azarnoff, D.L., Declaration of Daniel L. Azarnoff, M.D., including *Curriculum Vitae*, 27 pages, Oct. 3, 2003.

Benet, L.Z. et al., "Section 1: General Principles, Chapter 1: Pharmacokinetics: The Dynamics of Drug Absorption, Distribution, and Elimination" in *Goodman & Gilman's The Pharmacological Basis of Therapeutics*, 8th Ed., Pergamon Press, pp. 1-32 (1980).

Boughton-Smith, N.K., "Nitric Oxide Synthase Activity in Ulcerative Colitis and Crohn's Disease," The Lancet, 342:338-340 (1999).

Cellegy Pharmaceuticals Inc., "Corporate Alliances," 2 pages, undated.

Chaudhuri, G. et al., "NO is More Important than $PGI_2$ in Maintaining Low Vascular Tone in Feto-placental Vessels," Am. J. Physiol. 265 (Heart Circ. Physiol. 34):H2036-43 (1993).

Conant, C.C., "Plasma Nitroglycerin Levels, Blood Pressure and Apical Heart Rate Variations to Site of Application of Nitroglycerin Ointment," Nurse Practitioner 13(10):56-64 (1988).

Dollery, C.T., Declaration of Colin T. Dollery, MB, Ch.B. FRCP., including *Curriculum Vitae*, 63 pages, May 24, 2004.

ERBA, M. et al., "Nitropaste for Prevention and Relief of Vascular Spasm," AJNA, 10:155-56 (1989).

Flynn, G.L., Declaration of Gordon L. Flynn, Ph.D., including *Cirriculum Vitae*, 29 pages, May 21, 2004.

Flynn, G.L. "Topical Drug Absorption and Tropical Pharmaceutical Systems," Modern Pharmaceutics, 2d Ed., pp. 263-64, 89 (1990).

Gibbons, R.D., Declaration of Robert D. Gibbons, including *Curriculum Vitae*, 19 pages, May 13, 2002.

Hadgraft, J., "Recent Developments in Topical and Transdermal Delivery," Eur. J. Drug Metab. Pharmacokinetics 21(2):165-73 (1996).

King, D., Declaration of Denis King, 1 page, Dec. 23, 2000.

King, D.W., "GTN in the Management of Anal Fissure," presentation slides and cover letter, 9 pages, Mar. 7, 2001.

L'Hopital, F. et al., "Constipation et Hypertonle du Sphincter Interne de L'Anus: Response Sphincterienne A L'Administration Sub-Linguale de 0,40 Mg de Natispray," Gastroenterol Clin Biol 14:268 (1990) with English Translation.

Lipton, S.A. et al., "A Redox-based Mechanism for the Neuroprotective and Neurodestructive Effects of Nitric Oxide and Related Nitroso-compounds," Nature 364:626-32 (1993).

Lopez-Belmonte, J. et al., "The Actions of Nitric Oxide Donors in the Prevention or Induction of Injury to the Rat Gastric Mucosa," Br. J. Pharmacol. 108:73-78 (1993).

Lund, J.N., Declaration of Mr. Jonathan Lund, including *Curriculum Vitae*, 29 pages, Mar. 6, 2003.

Mahajan, R.P. et al., "Topical Nitroglycerin Prevents the Pressor Response to Tracheal Intubation and Sternotomy in Patients Undergoing Coronary Artery Bypass Graft Surgery," Anaestesia 48:297-300 (1993).

Matheis, G. et al., "Role of L-arginine-nitric Oxide in Myocardial Reoxygenation Injury," Am. J. Physiol. 262:H616-20 (1992).

Medical Economics, Physicians, *Physicians' Desk Reference*, 46 Edition, pp. 1004-1006; 1164-1166 (1992).

Merck & Co., Inc., "The Merck Manual of Diagnosis and Therapy, Section 3: Gastrointestinal Disorders, Chapter 35: Anorectal Disorders, General" retrieved online at <http://www.merck.com/mrkshared/mmanual/section3/chapter35/35a.jsp> on Feb. 14, 2005.

Parteq Innovations, "Cellegy Pharmaceuticals Acquires PARTEQ Spinoff Vaxis," 2 pages, Nov. 28, 2001.

Pavlick, K.P. et al., "Role of Reactive Metabolites of Oxygen and Nitrogen in Inflammatory Bowel Disease," Free Radical Biology & Medicine 33(3):311-322 (2002).

Piazza, C.T., Declaration of Christin T. Piazza, 2 pages, May 15, 2002.

Ranade, V.V., "Drug Delivery Systems. 6. Transdermal Drug Delivery," J. Clin. Pharmacol. 31:401-418 (1991).

Romanelli, M. et al., "The Effect of Topical Nitroglycerin on Transcutaneous Oxygen," British Journal of Dermatology 124:354-357 (1991).

Sandrini, A. et al., "Effect of Montelukast on Exhaled Nitric Oxide and Nonvolatile Markers of Inflammation in Mild Asthma," CHEST 124:1334-1340 (2003).

Scholefield, J.H. et al., "A Dose Finding Study with 0.1%, 0.2%, and 0.4% Glyceryl Trinitrate Ointment in Patients with Chronic Anal Fissures," Gut 52:264-69 (2003).

Scholefield, J.H., Declaration of John Howard Scholefield, including *Curiculum Vitae*, 47 pages, Feb. 28, 2005.

Schouten, W.R., "Pathophysiological Aspects and Clinical Outcome of Intra-Anal Application of Isosorbide Dinitrate in Patients with Chronic Anal Fissure," Gut 39(6):465-469 (1996).

Sherman, M. P., "Nitric Oxide-Mediated Neuronal Injury in Multiple Scierosis," Medical Hypotheses 39:143-146 (1992).

Shively, M., "Effect of Nitroglycerin Ointment Placement on Headache and Flushing in Healthy Subjects," Int. J. Nurs. Stud., 28(2):153-161 (1991).

Van Reempts, P. et al., "Topical Use of Nitroglycerin Ointment in Neonates" Editorial Correspondence, J. Pediatr, 116(1):155 (1990).

Weinhardt, J.A. "Making the Most of Topical Nitroglycerin," RN 48(12);38-40 (1985).

Anonymous, "ASCRS Registrants: 92nd Annual Convention - May 2-7, 1993, Hyatt Regency Chicago, Chicago, IL," List of Registrants, 34 pages [Exhibit PBL-9 to the Loder Declaration].

Anonymous, "Royal Australian College of Surgeons and Australian New Zealand College of Anaesthetists Annual Scientific Congress-Adelaide 1993: Statistics at May 14, 1993" and "A.S.C. Adelaide 1993 Scientific Programme: May 10-14, 1993" Proceeding excerpts, 5 pages [Exhibit PBL-11 to the Loder Declaration].

Brookes, S., "Statutory Declaration: In the Matter of Australian Patent Application No. 708694 in the Name of Cellegy Australia Pty Ltd -and- In the Matter of Opposition thereto by Peter Loder," 2 pages, Oct. 11, 2000.

Cristofani, K., "Anal fissures treated: Topical glyceryl trinitrate may play an important role in the management of anal fissures, US surgeons say," Australian Doc. Oct. 4, 1996.

Howes, L.G., "Statutory Declaration: In the Matter of Australian Patent Application No. 708694 in the Name of Cellegy Australia Pty Ltd -and- In the Matter of Opposition thereto by Peter Loder," 2 pages, Oct. 12, 2000, with Curriculum Vitae of Lawrence Guy Howes as Exhibit LGH-1 (26 pages).

Jones, I.T., "The solitary rectal ulser," presentation abstract, May 14, 1993 [Exhibit PBL-11 to the Loder Declaration].

Kamm, M.A. et al., "The Sir Alan Parks Physiology Unit," St. Mark's Hospital Year Book, St. Mark's Hospital, London, U.K., 2 pages [Exhibit PBL-14 to the Loder Declaration].

Kennedy, M.L., "Statutory Declaration: In the Matter of Australian Patent Application No. 708694 in the Name of Cellegy Australia Pty Lyd -and- In the Matter of Opposition thereto by Peter Loder," 2 pages, Oct. 12, 2000.

Loder, P.B., "Statutory Declaration: In the Matter of Australian Patent Application No. 708694 in the Name of Koren Laboratories Pty Limited -and- In the Matter of Opposition thereto Peter Loder," Oct. 11, 2000, 37 pages; with Exhibits PBL-2, 5, 8, 9, 11, 12,14, 19, and 22-25.

Loder, P.B., "Curriculum Vitae of Peter Bruce Loder" Oct. 11, 2000, 14 pages [Exhibit PBL-2 to the Loder Declaration].

Loder, P.B., "Application for Ethical Approval of Pilot Study" Oct. 11, 2000, 15 pages [Exhibit PBL-8 to the Loder Declaration].

Loder, P.B. et al., "Reversible chemical sphincterotomy by topical of glyceryl trinitrate (GTN)," St. Mark's Hospital, London, U.K., presentation abstract, May 13, 1993 [Exhibit PBL-11 to the Loder Declaration].

Loder, P.B. et al., "A new den for the winged lion: St. Mark'at Northwick Park," St. Mark's Hospital, London, U.K., presentation abstract, May 14, 1993 [Exhibit PBl-11 to the Loder Declaration].

Loder, P.B., Presentation Slides, May 13-14, 1993, 14 pages [Exhibit PBL-12 to the Loder Declaration].

Loder, P.B., Letter to Dr. D.Z. Lubowski re discussion of GTN, 2 pages, Jul. 18, 2000 [Exhibit PBL-22 to the Loder Declaration and Exhibit DZL-14 to the Lubowski Declaration].

Loder, P.D., Email message to John Scholefield re GTN + Warts, 2 pages, Aug. 1, 1998 [Exhibit PBL-23 to the Loder Declaration].

Loder, P.D., Type-written notes re telephone conversations with D.Z. Lubowski, Nov. 11, 1999 and Nov. 28, 1999, 2 pages [Exhibit PBL-25 to the Loder Declaration].

Lubowski, D.Z., "Statutory Declaration: In the Matter of Australian Patent Application No. 708694 in the Name of Cellegy Australia Pty Limited -and- In the Matter of Opposition thereto Peter Bruce Loder," Oct. 16, 2000, 14 pages; with Exhibits DZL-1, 9, and 14.

Lubowski, D.Z., "Curriculum Vitae of David Z. Lubowski," 38 pages, Oct. 16, 2000 [Exhibit DZL-1 to the Lubowski Declaration].

Lubowski, D.Z. et al., "A radio-isotope study of colonic function during defaecation," St. George Hospital, Sydney, presentation abstract, May 13, 1993 [Exhibit PBL-11 to the Loder Declaration].

Lubowski, D.Z., "Anorectal physiology - In it useful in rectal prolapse?," St. George Hospital, Sydney, presentation abstract, May 14, 1993 [Exhibit PBL-11 to the Loder Declaration].

Lubowski, D.Z., Letter to Dr. P.B. Loder re discussion of GTN with reply by Peter B. Loder, 3 pages, Jul. 25, 1998 [Exhibit DZL-14 to the Lubowski Declaration and Exhibit PBL-22 to the Loder Declaration].

Marchei, C., "Statutory Declaration: In the Matter of Australian Patent Application No. 708694 in the Name of Cellegy Australia Pty Ltd -and- In the Matter of Opposition thereto by Peter Loder," 2 pages, Oct. 11, 2000.

Phillips, R.K.S., Letter dated Oct. 29, 1998 and May 12, 1998 regarding invitation to lecture at St. Mark's Hospital, 7 pages [Exhibit DZL-9 to the Lubowski Declaration].

Scholefield, J., Email messages to Peter Loder, including 1 from Peter Stein, regarding Gorfine patent application, 4 pages, Apr. 1, 1997 [Exhibit PBL-19 to the Loder Declaration].

Schouten, W.R., "Lateral internal sphincterotomy in the treatment of Hemorrhoids: A Clinical and manometric study" Dis Colon Rectum 29:869-72 (1986) [Exhibit PBL-5 to the Loder Declaration].

Stein, P.M., Letter to Dr. Peter B. Loder regarding circumstances surrounding meeting, 3 pages, Sep. 18, 2000 [Exhibit PBL-24 to the Loder Declaration].

* cited by examiner

NITRIC OXIDE DONOR COMPOSITION AND METHOD FOR TREATMENT OF ANAL DISORDERS

CROSS-REFERENCES TO RELATED APPLICATIONS

This application is a continuation of U.S. application Ser. No. 10/021,168, filed on Dec. 11, 2001 now abandoned, which is a continuation of U.S. application Ser. No. 08/970,447, filed on Nov. 14, 1997 now abandoned, which is a continuation of U.S. application Ser. No. 08/666,264, filed on Jun. 20, 1996, now U.S. Pat. No. 5,693,676, which is a continuation of U.S. application Ser. No. 08/371,088, filed on Jan. 10, 1995, now abandoned, which is a continuation-in-part of U.S. application Ser. No. 08/250,555, filed on May 27, 1994, now U.S. Pat. No. 5,504,117. The disclosures of each of which are herein incorporated by reference in their entireties for all purposes.

BACKGROUND OF THE INVENTION

This invention is directed to a composition and method for treating anal disorders such as anal fissure, anal ulcer, hemorrhoidal disease and levator spasm, by topical application of the composition to or proximate the affected area.

In general, anal fissure (fissure-in-ano), anal ulcer, acute hemorrhoidal disease, and levator spasm (proctalgia fugax) are common, benign conditions of the anal canal which affect humans of all ages, races and sexes. However, these conditions can be problematical to treat and inconvenient if not painful to endure. An anal fissure or ulcer is a tear or ulcer of the mucosa or lining tissue of the distal anal canal. Anal fissure/ulcer can be associated with other systemic or local diseases but is more frequently present as an isolated finding. The typical, idiopathic fissure or ulcer is confined to the anal mucosa, and usually lies in the posterior midline, distal to the dentate line. The person with an anal fissure or ulcer frequently experiences anal pain and bleeding, the pain being more pronounced during and after bowel movements.

Hemorrhoids are specialized vascular areas lying subjacent the anal mucosa. Symptomatic hemorrhoidal disease is manifest by bleeding, thrombosis and/or prolapse of the hemorrhoidal tissues. Commonly, internal hemorrhoidal tissue bulges into the anal canal during defecation causing bleeding and pain. As the tissue enlarges, further bleeding and pain, prolapse and thrombosis can ensue. The thrombosis of hemorrhoids is another cause of bleeding and pain.

Levator spasm is a condition affecting women more frequently than men. This syndrome is characterized by spasticity of the levator ani muscle, a portion of the anal sphincter complex. The patient suffering from levator spasm may experience severe, episodic rectal pain. Physical exam may reveal spasm of the puborectalis muscle and pain may be reproduced by direct pressure on this muscle. Bleeding is normally not associated with this condition.

The underlying causes of these anal disorders are poorly understood, but all of these conditions are associated with a relative or absolute degree of anal sphincter hypertonicity. In the case of anal fissure/ulcer, the abnormality appears to be an as-yet-unidentified problem of the internal anal sphincter muscle. The internal sphincter is a specialized, involuntary muscle arising from the inner circular muscular layer of the rectum. Intra-anal pressure measurements obtained from people suffering from typical anal fissure/ulcer disease show an exaggerated pressure response to a variety of stimuli. The abnormally high intra-anal pressure is generated by the internal sphincter muscle and is responsible for non-healing of the fissure or ulcer and the associated pain.

An abnormal pressure response in the anal canal has also been observed in people suffering from symptomatic hemorrhoidal disease. Elevated intra-anal pressures may be a major factor in the development of this condition. It has been postulated that the pain associated with acute hemorrhoidal disease is caused in part by spasm of the internal anal sphincter muscle. Similarly, the pain associated with levator spasm is induced by the muscle spasm itself.

Various therapies have been devised to treat these anal disorders. Typical, non-surgical therapy includes bulk laxatives and sitz baths. Sitz baths are helpful because they induce relaxation of the anal sphincter mechanism. See e.g., Shafik, "Role of warm-water bath in anorectal conditions: The 'thermosphincteric reflex,'" *J. Clin. Gastroenterol.*, 16:304–308, 1993.

Topical anal therapy is also used in an effort to promote healing, relieve pain, and reduce swelling and inflammation. Many preparations have been tried including those containing local anesthetics, corticosteroids, astringents, and other agents. However, none of these preparations has been shown conclusively to reduce the healing time or to reliably ameliorate associated pain.

In certain instances, surgery may be employed to treat anal disorders. Cases of anal fissure/ulcer or hemorrhoids recalcitrant to medical therapy are often referred for surgical treatment. In keeping with the proposed etiology of anal fissure/ulcer, the current standard surgical procedure therefor is lateral internal anal sphincterotomy. In this procedure, the internal anal sphincter muscle is partially cut, thereby reducing the intra-anal pressure. The lowered pressure allows the fissure/ulcer to heal and also relieves the associated pain. Surgical hemorrhoidectomy removes the redundant hemorrhoidal tissue, and many surgeons will perform concomitant limited internal anal sphincterotomy to lower anal canal pressure. There is no successful surgical treatment for levator spasm.

Recently, a third component of the autonomic nervous system, known as the enteric nervous system (ENS), has been described and elucidated. This neural network innervates the gut continuously from esophagus to anus. It is composed of enteric neurons, and the processes of extrinsic efferent and afferent neurons of the traditional autonomic system. This system regulates the motor and secretory function of the gut. A notable feature of the ENS is the diversity of chemical messengers which enteric neurons contain and release. In addition to acetylcholine and norepinephrine, various peptide and non-peptide substances have been identified which appear to function as neurotransmitters in the ENS. Inhibitory non-adrenergic non-cholinergic (NANC) nerves are thought to be important therein.

More recently, nitric oxide (NO) has been identified as an inhibitory transmitter to muscle. It has been shown that NO mediates the anorectal inhibitory reflex in animals and man. See e.g., Rattan et al., "Nitric oxide pathway in rectoanal inhibitory reflex of opossum internal anal sphincter," *Gastroenterology*, 103:43–50, 1992; Chakder et al., "Release of nitric oxide by activation of nonadrenergic noncholinergic neurons of internal anal sphincter," *Am. J. Physiol.*, 264: G7–G12, 1993; O'Kelley et al., "Nerve mediated relaxation of the internal anal sphincter: The role of nitric oxide," *Gut*, 34:689–693, 1993. See also, Gillespie et al., "Influence of haemoglobin and erythrocytes on the effects of EDRF, a smooth muscle inhibitory factor, and nitric oxide on vascular and non-vascular smooth muscle," *Br. J. Pharmacol.*, 95:1151–1156, 1988; Ignarro et al., "Nitric oxide and cyclic GMP formation upon electrical field stimulation cause relaxation of corpus cavernosum smooth muscle," *Biochem. Biophys. Res. Commun.,* 170:843–850, 1990; Bult et al., "Nitric oxide as an inhibitory non-adrenergic non-cholinergic neurotransmitter," *Nature,* 345:346–347 1990. It has been proposed that NO formation, based upon non-enzymatic NO release from various organic nitrates as catalyzed in the presence of cysteine, causes direct or indirect activation of the soluble guanylate cyclase, finally resulting in relaxation of vascular smooth muscle in vivo. See, Feelisch et al., "Correlation between nitric oxide formation during degradation of organic nitrates and activation of guanylate cyclase," *Eur. J. Pharmacol.,* 139:19–30, 1987. See also Fung et al., "Biochemical mechanism of organic nitrate action," *Am. J. Cardiol.,* 70:4B–10B, 1992.

Organic nitrates such as nitroglycerin (GTN), isosorbide dinitrate (ISDN), isosorbide mononitrate (ISMN), erythrityl tetranitrate (ETN), pentaerythrityl tetranitrate (PETN) are known to cause vasodilation and have been used for decades in the treatment of angina pectoris. See e.g., Huff et al. (Eds.), "Physicians' Desk Reference," 41st Edition, Medical Economics Company, Oradell, N.J., 1987, at pages 780, 1176–78, 1533 and 1984–85; Rubin, U.S. Pat. No. 5,059,603 (October 1991); Budavari et al. (Eds.), "The Merck Index," 11th Edition, Merck & Co., Rahway, N.J., 1989, p. 821 (isopropyl nitrate); Fung et al., "Biochemical mechanism of organic nitrate action," *Am. J. Cardiol.,* 70:4B–10B, 1992.

Corticosteroids such as hydrocortisone have been used for the treatment of various benign anal disorders for many years. Studies of this treatment have show some benefit thereby but not in a reproducible nor significant fashion.

Topical anesthetics such as dibucaine, lidocaine, pramoxine, and others have been used for treatment of anal pain. However, any relief has been relatively short-lived.

Various other preparations are known. See e.g., Suzuki et al., U.S. Pat. No. 4,292,299 (September 1981), note column 5 lines 18–20 & 26–28; Rubin '603, note column 7, lines 61–65 & example 1; Greiner, U.S. Pat. No. 5,183,663 (February 1993). See also, Williams, U.S. Pat. No. 4,118,480 (October 1978); Huff et al. (Eds.), "The Merck Index," 11th Edition, page 198.

SUMMARY OF THE INVENTION

It is an object of the present invention to provide an effective treatment for anal diseases such as anal fissure, anal ulcer, hemorrhoidal disease, and levator spasm, which treatment includes the rapid relief of pain associated with such diseases.

It is another object of the invention to provide a composition containing an organic nitric oxide donor compound which can be employed in the treatment of such anal disease(s).

It is also an object of the invention to provide a method of treating such anal disease(s) by contacting the affected area with an effective amount of nitric oxide delivered by release from an organic nitrate.

It is a further object of this invention to provide a composition containing an organic nitric oxide donor compound in combination with a corticosteroid and/or topical anesthetic which can be employed in the treatment of such anal disease(s).

It is a still further object hereof to provide a method of treating such anal disease(s) by contacting the affected area with an effective amount of nitric oxide delivered by release from an organic nitrate plus a corticosteroid and/or topical anesthetic.

To accomplish these and other related objects of the invention, the present invention provides, in one aspect, a pharmaceutical composition useful for treating anal disease without debilitating side effects comprising an organic nitric oxide donor in combination with a carrier, optionally with a corticosteroid and/or topical anesthetic. In one embodiment, if the organic nitric oxide donor is only nitroglycerin and the composition is a soft paraffin or petroleum based ointment then the nitroglycerin is present in an amount excluding 0.5 percent by weight, and optionally also excluding 0.2, 1 and/or 2 percent by weight. All weight percents expressed herein are based on the total weight of the composition. In another aspect, the invention is directed to a method for treating an anal disease comprising contacting an appropriate anal area with an effective amount of nitric oxide, preferably delivered by release from an organic nitric oxide donor. The method may also include optional application of a corticosteroid and/or topical anesthetic to the anal area. The present invention is useful in treatment of anal disease, especially anal fissure, anal ulcer, hemorrhoids and levator spasm. In many patients treatment can be obtained without debilitating side effects. Notably, and perhaps most significantly, anal pain can be rapidly and effectively controlled with the composition of the present invention.

DETAILED DESCRIPTION OF THE INVENTION

All references cited in the present specification are incorporated herein by reference.

The role of nitric oxide in relaxation of the internal anal sphincter (IAS) in response to the rectoanal reflex has been studied in the opossum by others (see, Rattan S., Sarkar A., Chakder S., *Gastroenterology,* (1992 July), 103(1):43–50). They monitored resting pressures in the IAS using low-compliance continuously perfused catheters and reported the following.

L-NG-nitro-arginine (L-NNA), a NO-synthase inhibitor, caused significant dose-dependent suppression of the decrease in resting pressures in the IAS in response to the reflex mimicked by the rectal balloon distention. IAS relaxation in response not only to rectoanal reflex but also to other neural stimuli such as sacral nerve stimulation, local intramural stimulation, and the nicotinic ganglionic stimulant 1,1-dimethyl-4-phenylpiperazinium was also blocked by an NO-synthase inhibitor. The suppression of the neurally mediated IAS relaxation by L-NNA was stereoselective; D-NNA had no effect on the relaxation. The suppression of the rectoanal reflex-induced IAS relaxation by L-NNA was completely reversed by NO precursor L-arginine stereoselectively as D-arginine failed to reverse the suppressed IAS relaxation. The decrease in the resting pressure of the IAS caused by sodium nitroprusside was modified neither by the neurotoxin tetrodotoxin nor by L-NNA. Furthermore, the inhibitor of NO synthase did not modify the decrease in the resting pressure of the IAS by the direct-acting beta-adrenoceptor agonist isoproterenol. It was concluded that NO or a NO-like substance is an important mediator of IAS relaxation in response to noradrenergic, noncholinergic nerve stimulation.

Another study by others on the release of nitric oxide by activation of nonadrenergic noncholinergic neurons of internal anal sphincter has also been reported (see, Chakder S., Rattan S., *Am J. Physiol,* (1993 January), 264(1 Pt 1):G7–12.). This study investigated the direct release of nitric oxide (NO) in response to the stimulation of nonadrenergic noncholinergic (NANC) nerves. Isolated smooth muscle strips of the opossum (Didelphis virginiana) internal anal sphincter (IAS) were used. This study reported the following:

Electrical field stimulation (EFS) of these strips using the appropriate parameters was reported to cause a frequency-dependent fall in the resting tone of the IAS. The chemiluminescence method was used in the study to measure the release of NO. The stimulation of NANC neurons by the nicotinic stimulant 1,1-dimethyl-4-phenylpiperazinium (DMPP) and EFS caused IAS relaxation with an accompanying release of NO. The study found pretreatment of the smooth muscles with the neurotoxin tetrodotoxin and the NO-synthase inhibitor NG-nitro-L-arginine (L-NNA) abolished the release of NO and the fall in the resting tension of IAS in response to lower frequencies of EFS and DMPP. Addition of the NO precursor L-arginine reversed to control levels of the loss of the release of NO and the IAS relaxation in the presence of L-NNA. Again, the effect of L-NNA and L-arginine on NO release and IAS relaxation was stereoselective. D-NNA and D-arginine had no significant effect. The release of NO from IAS smooth muscle strips caused by vasoactive intestinal polypeptide was also abolished by L-NNA. However, both isoproterenol and atrial natriuretic factor caused IAS relaxation without any increase in NO release. These investigations show that NO is directly released in response to the stimulation of gut NANC inhibitory neurons.

An additional study of nerve mediated relaxation of the human internal anal sphincter investigated the role of nitric oxide. See, O'Kelly T., Brading A., Mortensen N., *Gut*, (1993 May) 34(5):689–93. This reference concerns whether nitric oxide (NO) is the non-adrenergic, non-cholinergic neurotransmitter which is released by enteric inhibitory nerves to mediate relaxation of the human internal anal sphincter. Isolated muscle strips were mounted in a superfusion organ bath so as to record their isometric tension. This study reported the following:

An exogenous donor of NO, sodium nitroprusside, relaxed the strips in a dose dependent manner. In the presence of atropine and guanethidine, transmural field stimulation produced relaxations. These relaxations were sensitive to tetrodotoxin. These relaxations were also inhibited in a concentration dependent and stereospecific manner by antagonists of NO synthase; completely by L-nitroarginine and partially by L-N-monomethyl arginine. These inhibitory effects were reversed by L-arginine. D-arginine did not reverse them. The relaxations were abolished by the nitric oxide scavenger, oxyhaemoglobin, but not methaemoglobin. The O'Kelly, et al. findings strongly indicated that NO is, or is very closely associated with, the non-adrenergic, non-cholinergic neurotransmitter which mediates the neurogenic relaxation of the human internal anal sphincter.

In general herein, the term "anal" includes musculature and vasculature tissue of or proximate the anus and/or lower gut. The term "anal disease" means a disorder of the tissue which may include musculature and/or vasculature of or proximate the anus and/or lower gut. The term "organic nitric oxide donor" means an organic compound or mixture of compounds with at least one of such compound(s) which can release nitric oxide under physiological or anal disease treatment conditions.

The present invention concerns treatment directed at the underlying cause of anal diseases which include, for example, anal fissure, anal ulcer, hemorrhoids and/or levator spasm. In general, the cause of these diseases is believed to be an unidentified abnormality of the anal sphincter muscles.

The compositions useful for treatment according to the present invention can be in suitable topical, including suppository, form. An appropriate physiologically acceptable carrier is utilized to contain the organic nitric oxide donor, optionally with other agent(s) such as a corticosteroid and/or a topical anesthetic. The methods of treating anal diseases in accordance with the present invention can employ nitric oxide from any suitable source.

The invention may be employed in therapeutic medicine with human patients. Preferably, the organic nitric oxide donor includes at least one organic nitrate, which include esters of nitric acid and may be an acyclic or cyclic compound, such as represented by the following general formula:

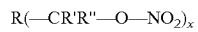

$$R(-CR'R''-O-NO_2)_x$$

wherein:
R is an organic or H (hydro) moiety or covalent bond, preferably a 2 to about 12 carbon hydrocarbon or oxygen-substituted hydrocarbon, especially one having 2 to 6 carbons and from 0 to 2 oxygen(s);
R' is an organic or hydro moiety or covalent bond, and preferably methyl; lower alkyl, to include ethyl, propyl, butyl, pentyl, and hexyl; methoxy; lower alkoxy; or hydro;
R" is an organic or hydro moiety or covalent bond, preferably methyl, lower alkyl, methoxy, lower alkoxy, or hydro, and especially hydro; and
x is an integer from 1 to about 12, and preferably from 2 to 6.

For instance, the organic nitrate may be ethylene glycol dinitrate; isopropyl nitrate; glyceryl-1-mononitrate; glyceryl-1,2-dinitrate; glyceryl-1,3-dinitrate; nitroglycerin (GTN); butane-1,2,4-triol-trinitrate; erythrityl tetranitrate (ETN); pentaerythrityl tetranitrate (PETN); isosorbide mononitrate (ISMN), which may include isosorbide-2-mononitrate (IS2N) and/or isosorbide-5-mononitrate (IS5N); and/or isosorbide dinitrate (ISDN), and so forth and the like. An advantageous organic nitrate is GTN, and advantageous other organic nitrates include ISDN, ETN, PETN, etc., which may have been given regulatory approval for use in treatments in other fields of medicine on human subjects.

In general, the organic nitric oxide donor, to include the organic nitrate, is present in any amount which is effective in the practice of the treatment of anal disease. In typical practice of the invention the organic nitric oxide donor can be present in a concentration from about 0.01 to about 10 percent by weight. All weight percentages herein are based on the total weight of the composition. If GTN is the organic nitrate, preferred concentrations reside in the range of from about 0.01 to about 5 percent by weight. The following table lists some more particular general ranges for other organic nitrates in compositions of the invention:

| Compound | Approximate Weight Percents |
|---|---|
| ISDN | 0.01 to 7.5, to include 0.3 to 3 |
| ETN | 0.01 to 4, to include 0.1 to 1.5 |
| PETN | 0.01 to 4, to include 0.1 to 1.5 |

Optionally, a corticosteroid may be present in the compositions of the present invention. For instance, the corticosteroid may include hydrocortisone, i.e., 11-17-21-trihydroxypregn-4-ene-3,20-dione or cortisol, cortisol acetate, hydrocortisone phosphate, hydrocortisone 21-sodium succinate, hydrocortisone tebutate, corticosterone, corticosterone acetate, cortisone, cortisone acetate, cortisone 21B-cyclopentanepropionate, cortisone phosphate, triamcinolone hexacetonide, dexamethasone phosphate, desonide, betamethasone dipropionate, mometasone furate, and so forth and the like.

In general, the corticosteroid may be present in any amount which is effective in the practice of the treatment of anal disease. In typical practice of the invention, the corticosteroid can be present in a concentration from about 0.001 to about 10 percent by weight and preferably from about 0.1 to about 5 percent by weight. If cortisol is the corticosteroid, preferred concentrations reside in the range of from about 0.5 to about 2.5 percent by weight. If hydrocortisone is the corticosteroid, preferred concentrations reside in the range of from about 0.5 to about 5 percent by weight. If dexamethasone phosphate is the corticosteroid, preferred concentrations reside in the range of from about 0.005 to about 0.03 percent by weight.

Optionally, a topical anesthetic may be present in the composition of the invention. For instance, the topical anesthetic may include dibucaine, lidocaine, pramoxine, benzocaine, tetracaine, and so forth and the like. In general, the topical anesthetic may be present in any amount which is effective in the practice of the treatment of anal disease. In typical practice of the invention, the topical anesthetic can be present in a concentration from about 0.1 to about 5 percent by weight and preferably from about 0.5 to about 4 percent by weight based on the total weight of the composition. If dibucaine is the topical anesthetic, preferred concentrations reside in the range of from about 0.25 to about 2 percent by weight. If benzocaine is the topical anesthetic, preferred concentrations reside in the range of from about 10 to about 20 percent by weight. If tetracaine is the topical anesthetic, preferred concentrations reside in the range of from about 1 to about 2 percent by weight.

The corticosteroid and topical anesthetic may be employed together in the practice of the invention.

As those skilled in the art can appreciate, the composition of the invention may be formulated in any pharmaceutical state suitable for topical application, examples of which include liquid, aerosol, thickened liquid, emulsion, semisolid, powder, and a tablet or capsule, which may be lubricated for insertion into the anus. The method of the invention may employ any of such formulations as may be appropriate for treatment in particular cases. Advantageously, the composition can be formulated into highly convenient dosage forms with thickening agents to include thickened solutions or lotions, ointments to include creams and gels, and so forth.

Thickened solutions or lotions and ointments may be formed by incorporating with the active ingredients various gelling agents or other thickeners (viscosity increasers) which permit release of the active ingredients to the skin or tissue upon or following application. These forms are advantageously employed to lessen the runoff from the skin or tissue which may occur with more fluid (less viscous) formulations. Importantly, they also permit more sustained contact of the active ingredient(s) and any penetration enhancer with the treated surfaces, thus permitting an enhancement of the speed of delivery of the active ingredient(s) subcutaneously, and providing more accurate and controllable dosing. Accidental spilling and undesired contact with the composition can also be minimized with such types of formulations.

It can be advantageous to employ water-dispersible thickening agents, i.e., agents dispersible in water to form a homogeneous distribution or even solution, such as the polyethylene glycols and similar agents, as they are readily compatible with water or other diluents which may be formulated in the composition. Alternatively, an emulsion base may be employed to impart the desired thickening effect, together with the emollient effect of the lipoid phase of the emulsion base.

Water-soluble or water-dispersible thickening bases or substances may employ polyethylene glycols and the like of different viscosities depending upon the desired consistency and concentration of active ingredient(s) which may be incorporated into the composition. Other thickening agents which may be suitable for employment herein include but are not limited to water-dispersible gums, carboxyvinyl polymers, methyl cellulose, sodium carboxymethyl cellulose, and alginates.

Lotions and ointments incorporating emulsion bases may contain the usual ingredients to provide the base, including fatty alcohols such as acetyl alcohol, an emulsifier such as, for example, lauryl sulfate, and water. Also, the remainder of a topical preparation may contain one or more conventional ointment components such as, for example, white petrolatum, lanolin, distilled water, and mineral oil in conventional amounts. The remainder of a suppository may contain conventional amounts of known suppository components such as, for example, zinc oxide and/or cocoa butter.

Pourable pharmaceutical dosages may be provided and dispensed in graduated containers, or in containers which contain a given volume, say, for example, 5 or 10 cc, and so forth. Containers with greater volumes, say, for example, of 20 cc and greater, can provide convenient multiple dosage forms. Containers containing a typical single dose, for example, from about 0.5 g to about 10 g of active ingredient(s), can provide convenient dosage forms. Squeeze tubes for lotions and ointments and cotton stick applicators may be employed for topical application of the composition for liquids ranging from those of water-like viscosity to the more viscous formulations of thickened compositions and for powders and the like.

Dusts may be employed. An inert ingredient such as, for example, starch and/or talc may be employed to dilute the active ingredient(s) in powder form.

The composition of the invention, and the ingredient(s) in a method, may also be administered by dusting, spraying or misting such as from shakers, dusting devices, misting devices and aerosol bottles. Containers of the composition may be charged with any suitable amount and concentration of ingredient(s). As an illustration, a container may be charged with a fluid formulation containing at least about 10 percent by weight of a combination of active ingredients, along with an aqueous diluent, optionally with thickening agent(s), physiological salt(s), and so forth. Liquid compositions, for example, may be administered as low viscosity substances to semisolid gels or mousses, depending on any amount of gelling agent(s) and/or surfactant(s) included therein. Such compositions can be sufficiently fluid to permit their dispensing by spray or mist from the container and also can meet criteria for penetrability.

In treatment according to the invention, an amount of active ingredient(s) or composition of the invention is contacted with or applied to the affected anal area or proximate thereto such that an effective amount of nitric oxide, preferably delivered by release from an organic nitric oxide donor, is administered. The amount of active ingredient(s) or composition which is employed should be effective for the amelioration, control and/or healing of the anal disease and the prompt and dramatic control or relief of pain resulting from or associated with the disease. For example, an ointment composition of the invention can be applied topically at each application to the external anus and to the distal anal canal with the finger or an applicator. As an illustrative alternative, the medication can be delivered intra-rectally as a suppository. The medication can be applied in this fashion, for example, three or more times daily in the case of the ointment or once or more times daily in the case of the suppository.

Employment of the optional corticosteroid and/or topical anesthetic in the practice of the invention can provide decidedly advantageous results. In cases where treatment with an organic nitrate alone as active treating agent fails to provide relief from pain and/or healing, most notably, the employment of the corticosteroid and/or topical anesthetic in combination with the organic nitrate often can provide significant if not complete relief from pain and provide for significant if not total healing as well.

Pain relief from the invention is rapid and often dramatic.

The following examples further illustrate the present invention. All parts and percentages (percent or %) therein are by weight, unless otherwise specified.

EXAMPLE 1

An ointment was prepared by admixing 12.5 g of 2 percent nitroglycerin in white petrolatum, lanolin, and distilled water (nitroglycerin ointment, USP 2%; E. Fougera & Co., Melville, N.Y.) with 37.5 g white petrolatum, USP (VASELINE; Chesebrough-Ponds USA Co., Greenwich, Conn.) in a laboratory mixing vessel at room temperature. The resulting mixture was 50 g of a 0.5 percent nitroglycerin ointment.

EXAMPLE 2

An ointment of 12.5 g of 2 percent nitroglycerin in white petrolatum, lanolin, and distilled water (nitroglycerin ointment, USP 2%; E. Fougera & Co., Melville, N.Y.) was admixed with 20 g of 2.5 percent hydrocortisone in white petrolatum and light mineral oil (hydrocortisone ointment, USP 2.5%; Clay-Park Labs, Inc., Bronx, N.Y.) and with 17.5 g of white petrolatum, USP (VASELINE; Chesebrough-Ponds USA Co., Greenwich, Conn.) in a laboratory mixing vessel at room temperature. The resulting mixture was 50 g of a 0.5 percent nitroglycerin and 1 percent hydrocortisone ointment.

EXAMPLE 3

An ointment of 12.5 g of 2 percent nitroglycerin in white petrolatum, lanolin, and distilled water (nitroglycerin ointment, USP 2%: E. Fougera & Co., Melville, N.Y.) was admixed with 25 g of 1 percent dibucaine, USP, in white petrolatum, light mineral oil, acetone sodium bisulfite, lanolin, and purified water (NUPERCAINAL; Ciba Consumer Pharmaceuticals, Edison, N.J.) and with 12.5 g of white petrolatum, USP (VASELINE; Chesebrough-Ponds USA Co., Greenwich, Conn.) in a laboratory mixing vessel at room temperature. The resulting mixture was 50 g of a 0.5 percent nitroglycerin and 0.5 percent dibucaine ointment.

EXAMPLE 4

An ointment of 2.5 g of 2 percent nitroglycerin in white petrolatum, lanolin, and distilled water (nitroglycerin ointment, USP 2%; E. Fougera & Co., Melville, N.Y.) was admixed with 20 g of 2.5 percent hydrocortisone in white petrolatum and light mineral oil (hydrocortisone ointment, USP 2.5%; Clay-Park Labs, Inc., Bronx, N.Y.) and with 25 g of 1 percent dibucaine, USP, in white petrolatum, light mineral oil, acetone sodium bisulfite, lanolin, and purified water (NUPERCAINAL; Ciba Consumer Pharmaceuticals, Edison, N.J.) and with 2.5 g of white petrolatum, USP (VASELINE; Chesebrough-Ponds USA Co., Greenwich, Conn.) in a laboratory mixing vessel at room temperature. The resulting mixture was 50 g of a 0.5 percent nitroglycerin, 1 percent hydrocortisone, and 0.5 percent dibucaine ointment.

EXAMPLE 5

A 29-year old female had a 7-day history of anal pain and bleeding with bowel movements. Physical exam showed posterior midline anal fissure. The patient rated her pre-treatment pain 7/10. The patient applied approximately 500 mg of the ointment as prepared in Example 1, three times daily and after bowel movements. The patient reported that her pain was gone following initial application. After two weeks of treatment, the fissure had healed completely.

EXAMPLE 6

A 40-year old female had a 3-month history of anal pain and bleeding with bowel movements. Physical examination showed a superficial posterior midline anal fissure. The patient rated her pre-treatment pain 7/10. The patient applied approximately 500 mg of the ointment as prepared in Example 1, three times daily and after bowel movements. After one week of treatment, the patient noted persistent bleeding, but her pain was rated 2/10. After three weeks of treatment, the fissure was healed, and the pain was gone.

EXAMPLE 7

A 36-year old man had a 2-year history of anal pain and bleeding with bowel movements. Examination showed a posterior midline anal ulcer. Pre-treatment pain was rated 9/10. The patient was treated with hydrocortisone/pramoxine cream (ANALPRAM-HC, 2.5%; Ferndale Laboratories, Inc., Ferndale, Mich.) three times daily and following bowel movements. After one week of treatment, the patient rated his pain 6/10, and the physical condition was essentially unchanged. The patient was then treated with approximately 500 mg of the ointment as prepared in Example 2, three times daily and after bowel movements. He reported "immediate" relief of pain with each application. After one week of such therapy, the ulcer was smaller, but not yet completely healed.

EXAMPLE 8

A 23-year old female had a 1-month history of anal pain and bleeding with bowel movements. Examination showed a superficial posterior midline anal fissure. She had previously failed a course of hydrocortisone therapy. Pre-treatment pain was rated 9/10. The patient was treated with approximately 500 mg of the preparation of Example 1, three times daily and after bowel movements. After one week of treatment, the fissure was still present, and pain was rated 8/10. The patient was then treated with approximately 500 mg of the preparation of Example 2, three times daily and after bowel movements. Following one week of therapy with the ointment as of Example 2, the patient reported no pain and no bleeding. Subsequent examination showed that the fissure had healed.

EXAMPLE 9

A 27-year old female had a 3-day history of anal pain and bleeding with bowel movements. Physical examination showed a superficial anterior midline anal fissure. Pretreatment pain was rated 4/10. The patient was treated with the ointment as of Example 2, approximately 500 mg three times daily and after bowel movements. Following one week of therapy, the patient reported that her pain had diminished, and it was rated 2/10. Examination showed improvement. After another fifteen days of therapy, the patient was pain free, and the fissure had healed.

EXAMPLE 10

A 27-year old man presented with a 5-day history of anal pain. Physical examination revealed a 1-cm thrombosed external hemorrhoid in the left anterolateral anal quadrant. The patient was treated with the ointment as of Example 3, approximately 500 mg three times daily and after bowel movements. He reported a significant reduction in anal pain and throbbing three days later.

EXAMPLE 11

A 57-year old man was referred for treatment of documented levator spasm which developed following lower spinal surgery two years before. The patient was treated with the ointment as of Example 1, approximately 500 mg intra-anally three times daily and after bowel movements. He reported improvement of the anorectal spasm within one day. Treatment was then switched to the preparation of Example 3, approximately 500 mg intra-anally three times daily and after bowel movements. Pain relief was not as great, and so, treatment with the preparation as of Example 1 was restarted.

EXAMPLE 12—GROUP STUDIES

METHODS

TEH Group: Five patients (three women and two men) were recruited to participate in a trial of topical nitroglycerin treatment for acutely thrombosed external hemorrhoids (TEH). Their ages ranged from 23 to 51 years old. The duration of their symptoms ranged from 2 to 4 days. Anorectal examination of all of these patients revealed TEH in one anal quadrant (three patients) and in two anal quadrants (two patients). None of these patients had evidence of internal hemorrhoid thrombosis, fissure, abscess, or fistula. All of these patients had used one or more topical preparations (ANUSOL or ANUSOL-HC, Parke-Davis, Morris Plains, N.J.; PREPARATION H, Whitehall Laboratories, Madison, N.J.; PROCTOCREAM-HC, Reed & Carnrick, Jersey City, N.J.) without symptomatic relief.

Fissure Group: Fifteen patients (ten women and five men) were recruited to participate in a trial of topical nitroglycerin treatment for anal fissure or ulcer. Their ages ranged from 23 to 61 years old. The duration of their symptoms ranged from 2 days to 2 years. Three patients had posterior midline anal ulcers; eleven had acute, posterior midline fissures; one had an acute, anterior midline anal fissure. Two patients had a history of Crohn's ileitis. None of these patients had a history of recent anal surgery.

After obtaining informed consent from each participant, a program of therapy was begun. Treatment included psyllium seed (12 g daily) and sitz baths as needed. Approximately 500 to 1000 mg of 0.5 percent nitroglycerin ointment as in Example 1 was applied with the finger to the external anus and distal anal canal four or more times daily and after bowel movements. All patients were interviewed and examined one week after initiating the therapy. Patients of the fissure group were re-examined three weeks after initiating therapy, and every one week or two weeks thereafter until either the fissure had healed or eight weeks of the therapy had passed.

RESULTS

TEH Group: All patients reported total or near total relief of anal pain within 2 to 3 minutes of nitroglycerin application. The nitroglycerin was especially useful in relieving the pain which typically occurred following defecation. Each application of the nitroglycerin ointment relieved anal pain from 4 to 6 hours in all patients. All patients reported the need for fewer sitz baths. The nitroglycerin ointment was used for an average of three days (range two to six days). Resolution of the thrombus appeared to follow the usual time course. Side effects were limited to transient headache in two patients (40 percent of the group population).

Fissure Group: All patients reported dramatic relief of anal pain within 3 to 4 minutes of application of the nitroglycerin ointment, and the effect of pain relief was sustained from 2 to 6 hours. Most patients reported that the nitroglycerin ointment was especially useful in relieving the pain that occurred following defecation. Fourteen patients applied the ointment every four to six hours while awake. One patient required application every two to three hours to achieve satisfactory pain control. Of the twelve with superficial anal fissures, ten (83 percent of this set) were healed within two weeks, and this set included the two patients with Crohn's disease. Two patients who had discontinued treatment after complete healing at two weeks had recurrences of their fissures. Both responded to another two weeks of therapy with no further recurrence of symptoms. The remaining two patients with anal fissures healed after four weeks of continuous treatment. One patient with a posterior anal ulcer was improved but not completely healed after two weeks of therapy. She requested sphincterotomy which resulted in complete healing within another month. Two patients with posterior anal ulcers were improved but not completely healed after two months of therapy, and sphincterotomy was refused in both cases. Side effects were limited to mild, transient headaches in five patients (33 percent of the group population).

The twenty patients in this study experienced dramatic pain relief after the first dose of the topically applied nitroglycerin ointment, and healing was significant. The nitroglycerin ointment topically applied to the anal and rectal area was well tolerated by most patients in this study. Seven of the twenty human subjects (35 percent of the groups population) experienced headaches after topical application of the nitroglycerin ointment. The headaches were generally self-limited and abated after about fifteen minutes.

EXAMPLE 13

An ointment is prepared by admixing 8.75 g of 2 percent nitroglycerin in white petrolatum, lanolin, and distilled water (nitroglycerin ointment, USP 2%; E. Fougera & Co., Melville, N.Y.) with 41.25 g white petrolatum, USP (VASELINE; Chesebrough-Ponds USA Co., Greenwich, Conn.) in a laboratory mixing vessel at room temperature. The resulting mixture is 50 g of a 0.35 percent nitroglycerin ointment.

The ointment is effective in the treatment of anal disease when applied topically to or proximate the affected area. Therewith, pain relief and healing are significant, and side effects such as headache are few and/or mild. The ointment can be employed with humans.

CONCLUSION

From the foregoing, it will be seen that this invention is one well adapted to attain all the ends and objects hereinabove set forth.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth is to be interpreted as illustrative and not in a limiting sense.

What is claimed is:

1. A method for ameliorating pain in a human patient associated with an anal disorder selected from one or more of the group consisting of anal fissure, anal ulcer, and hemorrhoidal disease, comprising administering an effective amount of an organic nitric oxide donor proximate to, or to, the affected area of the patient, and wherein said method the pain is ameliorated.

2. The method of claim 1, wherein said anal disorder is an anal fissure or ulcer.

3. The method of claim 1, wherein said anal disorder is hemorrhoidal disease.

4. The method of claim 1, wherein the organic nitric oxide donor is capable of releasing nitric oxide under physiological conditions.

5. The method of claim 4, wherein the administering is topical and the nitric oxide donor is formulated as an ointment, a cream, a gel, or a lotion.

6. The method of claim 5, wherein the organic nitric oxide donor is applied to a hemorrhoid.

7. The method of claim 5, wherein the organic nitric oxide donor is applied to an anal fissure or anal ulcer.

8. The method of claim 4, wherein the administering is topical and the nitric oxide donor is formulated as a liquid or semisolid.

9. The method of claim 4, wherein the nitric oxide donor is formulated as a suppository.

10. The method of claim 4, wherein the organic nitric oxide donor is formulated in a composition comprising the nitric oxide donor in an amount from 0.0 1% to 10% by weight and a physiologically acceptable carrier.

11. The method of claim 1, wherein the organic nitric oxide donor is capable of releasing nitric oxide under anal disease treatment conditions.

12. The method of claim 1, wherein the administering is topical.

13. The method of claim 1, wherein the administering is via a suppository.

14. The method of claim 1, wherein the organic nitric oxide donor is applied proximate to the affected area of the patient.

15. The method of claim 1, wherein the organic nitric oxide donor is applied to the affected area of the patient.

16. The method of claim 1, wherein the organic nitric oxide donor is formulated in a composition comprising the nitric oxide donor in an amount from 0.01% to 10% by weight and a physiologically acceptable carrier.

17. The method of claim 16, wherein the composition further comprises a carrier selected from the group consisting of white petrolatum, mineral oil, lanolin, distilled water, acetone, and cocoa butter.

18. The method of claim 16, wherein the composition further comprises a corticosteroid.

19. The method of claim 16, wherein the composition further comprises a local anesthetic.

20. The method of claim 16, wherein the composition is formulated as an ointment, a cream, a gel, or a lotion.

21. The method of claim 16, wherein the composition is formulated as a liquid or semisolid.

22. The method of claim 16, wherein the composition is formulated as a suppository.

23. A method of treating a human patient having pain associated with an anal fissure, anal ulcer, or hemorrhoid, comprising applying a composition comprising an effective amount of an organic compound which can release nitric oxide under physiological or anal disease treatment conditions and a physiologically acceptable carrier to an area proximate to, or to, the affected area-of the patient, wherein said method the pain is ameliorated.

24. A method of claim 23, wherein the affected area has a hemorrhoid.

25. A method of claim 23, wherein the affected area has an anal ulcer or anal fissure.

26. A method of claim 23, wherein the organic compound is formulated as a suppository.

* * * * *